US009753270B2

(12) United States Patent
Furuta

(10) Patent No.: US 9,753,270 B2
(45) Date of Patent: Sep. 5, 2017

(54) ILLUMINATION DEVICE

(71) Applicant: OLYMPUS CORPORATION, Tokyo (JP)

(72) Inventor: Koichiro Furuta, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/973,086

(22) Filed: Dec. 17, 2015

(65) Prior Publication Data
US 2016/0103312 A1 Apr. 14, 2016

Related U.S. Application Data

(63) Continuation of application No. PCT/JP2014/067362, filed on Jun. 30, 2014.

(30) Foreign Application Priority Data

Jul. 9, 2013 (JP) .................. 2013-143680

(51) Int. Cl.
A61B 1/06 (2006.01)
G02B 23/24 (2006.01)
G02B 23/26 (2006.01)
A61B 1/00 (2006.01)
A61B 1/07 (2006.01)

(52) U.S. Cl.
CPC ...... G02B 23/2469 (2013.01); A61B 1/00096 (2013.01); A61B 1/00165 (2013.01);
(Continued)

(58) Field of Classification Search
CPC ............... G02B 23/2469; G02B 23/26; A61B 1/00096; A61B 1/00165; A61B 1/0615; A61B 1/0607
See application file for complete search history.

(56) References Cited

U.S. PATENT DOCUMENTS

2004/0236231 A1 11/2004 Knighton et al.
2008/0242935 A1 10/2008 Inoue
(Continued)

FOREIGN PATENT DOCUMENTS

EP 0424272 A2 4/1991
EP 1685790 A1 8/2006
(Continued)

OTHER PUBLICATIONS

International Search Report, dated Sep. 22, 2014, issued in corresponding International Application No. PCT/JP2014/067362.
(Continued)

Primary Examiner — Thomas M Sember
(74) Attorney, Agent, or Firm — Andrews Kurth Kenyon LLP

(57) ABSTRACT

An illumination device includes a light output unit having an output end; an optical member that is disposed in a circumferential direction centered on a predetermined axis and that receives illumination light output from the output end and outputs the illumination light from a surface thereof; and a reflective layer that is provided adjacent to an inner side surface of the optical member and that reflects the illumination light outward in the radial direction. The optical member includes a light guide layer that receives the illumination light from the output end and that guides the illumination light and a diffusion layer that is located outside the light guide layer in the radial direction and at one end of the light guide layer in a direction along the axis and that receives the illumination light from the light guide layer and guides the illumination light while diffusing the illumination light.

12 Claims, 9 Drawing Sheets

(52) U.S. Cl.
CPC .......... *A61B 1/0607* (2013.01); *A61B 1/0615* (2013.01); *G02B 23/26* (2013.01); *A61B 1/0623* (2013.01); *A61B 1/07* (2013.01)

(56) References Cited

U.S. PATENT DOCUMENTS

| | | |
|---|---|---|
| 2011/0184244 A1 | 7/2011 | Kagaya et al. |
| 2012/0051693 A1 | 3/2012 | Yoshida et al. |
| 2012/0095292 A1 | 4/2012 | Gunday et al. |
| 2014/0071691 A1 | 3/2014 | Ito et al. |

FOREIGN PATENT DOCUMENTS

| | | |
|---|---|---|
| EP | 2 649 923 A1 | 10/2013 |
| EP | 2716967 A1 | 4/2014 |
| JP | H11-76148 A | 3/1999 |
| JP | 2004-329700 | 11/2004 |
| JP | 2008-237790 A | 10/2008 |
| JP | 2011-147757 A | 8/2011 |
| JP | 2011-152371 A | 8/2011 |
| JP | 2012-50607 A | 3/2012 |
| JP | 2012-55342 A | 3/2012 |
| WO | 2005/120330 A1 | 12/2005 |
| WO | 2012-137737 A1 | 10/2012 |
| WO | 2012-165347 A1 | 12/2012 |

OTHER PUBLICATIONS

Extended European Search Report, dated Jan. 31, 2017, from corresponding European Application No. 14822339.9.

ILLUMINATION DEVICE

CROSS-REFERENCE TO RELATED APPLICATIONS

This is a continuation of International Application PCT/JP2014/067362, with an international filing date of Jun. 30, 2014, which is hereby incorporated by reference herein in its entirety. This application claims the benefit of Japanese Patent Application No. 2013-143680, filed on Jul. 9, 2013, the content of which is incorporated herein by reference.

TECHNICAL FIELD

The present invention relates to illumination devices, and particularly to an illumination device for use with endoscopes having viewing angles of 180° or more.

BACKGROUND ART

There is a known endoscope that has a wide viewing angle, i.e., 180° or more, and that allows simultaneous observation of forward, side, and even backward fields of view (see, for example, patent literature PTL 1 below). For example, if an endoscope having a viewing angle of 180° or more is used in the large intestine, where numerous folds are found, the back side of a fold can be observed without changing the orientation of the distal end of the endoscope by a large amount, which allows the user to manipulate the endoscope more easily and to find an affected area more reliably. The endoscope in PTL 1 has, at the distal end thereof, an illumination device including two light guides and illuminates forward and side fields of view with different light guides to illuminate a wide field of view in its entirety.

Endoscopes have various components concentrated at the tips thereof, including image-capturing optical systems for capturing images of subjects, channels for surgical instruments, nozzles for lens cleaning, and mechanisms for bending bending sections thereof. Accordingly, there is a need for an illumination device that can be installed in a thin endoscope within the minimum possible space in the radial direction. The illumination device in PTL 1 includes a plurality of light guides arranged side-by-side in the radial direction in the surrounding part of the image-capturing optical system, and the distal end of the light guide for side illumination is bent in the radial direction of the endoscope to achieve side illumination. This requires a large installation space in the radial direction of the endoscope and thus results in a large increase in the tip diameter of the endoscope.

CITATION LIST

Patent Literature

{PTL 1}
Japanese Unexamined Patent Application, Publication No. 2004-329700

SUMMARY OF INVENTION

A first aspect of the present invention is an illumination device including a light output unit having an output end that outputs illumination light; an optical member that is disposed in a circumferential direction centered on a predetermined axis and that receives the illumination light from the output end and outputs the illumination light from a surface thereof; and a reflective layer that is provided adjacent to a surface of the optical member at an inner side in a radial direction and that reflects the illumination light outward in the radial direction. The optical member includes a light guide layer and a diffusion layer located outside the light guide layer in the radial direction and at one end of the light guide layer facing away from the output end of the light output unit in a direction along the predetermined axis. The light guide layer receives the illumination light from the output end and guides the illumination light. The diffusion layer receives the illumination light from the light guide layer and guides the illumination light while diffusing the illumination light.

A second aspect of the present invention is an illumination device including a light output unit having an output end that outputs illumination light; an optical member that is disposed in a circumferential direction centered on a predetermined axis and that receives the illumination light from the output end and outputs the illumination light from a surface thereof; and a reflective layer that is provided inside a surface of the optical member at an inner side in a radial direction and that reflects the illumination light outward in the radial direction. The optical member includes a light guide layer and a diffusion layer located outside the light guide layer in the radial direction and at one end of the light guide layer facing away from the output end of the light output unit in a direction along the predetermined axis. The light guide layer receives the illumination light from the output end and guides the illumination light. The diffusion layer receives the illumination light from the light guide layer and guides the illumination light while diffusing the illumination light.

DESCRIPTION OF EMBODIMENTS

{First Embodiment}

An illumination device 100 according to a first embodiment of the present invention will be described below with reference to FIGS. 1A to 6.

Figure 1A:
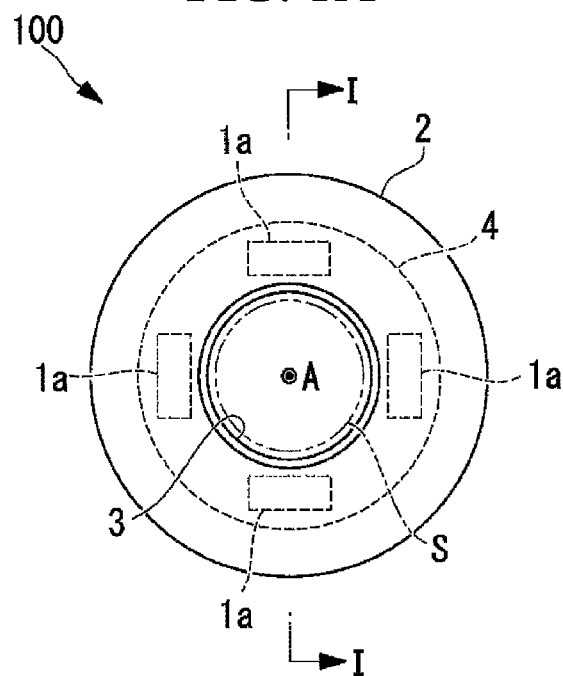
FIG. 1A is a front view showing the overall configuration of an illumination device according to a first embodiment of the present invention.
Figure 1B:
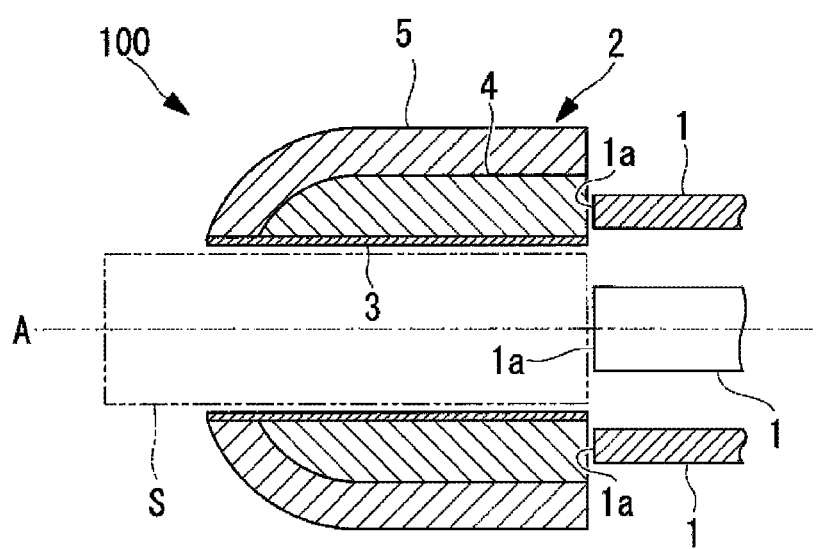
FIG. 1B is a longitudinal sectional view, taken along line I-I, of the illumination device in FIG. 1A.

As shown in FIGS. 1A and 1B, the distal-end portion of the illumination device 100 according to this embodiment (i.e., a portion composed of an optical member 2 and a reflective layer 3, described later) has a cylindrical structure and is exposed to the outside so as to circumferentially surround an image-capturing optical system provided at the distal end of an endoscope. In the same figures, the space S enclosed by the two-dot chain line represents the space where the image-capturing optical system is disposed, and the axis A represents the observation optical axis of the image-capturing optical system. In particular, the illumination device 100 according to this embodiment is designed for endoscopes including image-capturing optical systems having viewing angles of 180° or more and capable of simultaneously capturing images of fields of view forward (in the drawings, in the direction from right to left) and sideward of the observation optical axis A.

Specifically, as shown in FIGS. 1A and 1B, the illumination device 100 includes light output units 1 having output ends 1a that output illumination light, a substantially cylindrical optical member 2 that is provided at the distal ends of the light output units 1 and that receives the illumination light from the output ends 1a, guides the illumination light while diffusing it, and outputs the illumination light from a surface thereof, and a reflective layer 3 provided on the inner circumferential surface of the optical member 2.

The light output units 1 are, for example, fiber bundles disposed inside the endoscope. The proximal ends of the fiber bundles are connected to a light source unit (not shown) disposed outside the endoscope, and illumination light supplied from the light source unit is guided through the fiber bundles and is output from the distal ends of the fiber bundles, i.e., from the output ends 1a. The output ends 1a are located opposite the proximal-end surface of the optical member 2 in sufficient proximity thereto and direct the illumination light into the proximal-end surface of a light guide layer 4 (described later) of the optical member 2.

The color of the illumination light may be selected, as appropriate, depending on the application, preferably white for normal observation of subjects. For special light observation such as narrow-band imaging (NBI) and fluoroscopy, the illumination light may be narrow-band light, i.e., light having its emission spectrum only in a particular wavelength band.

Figure 2:
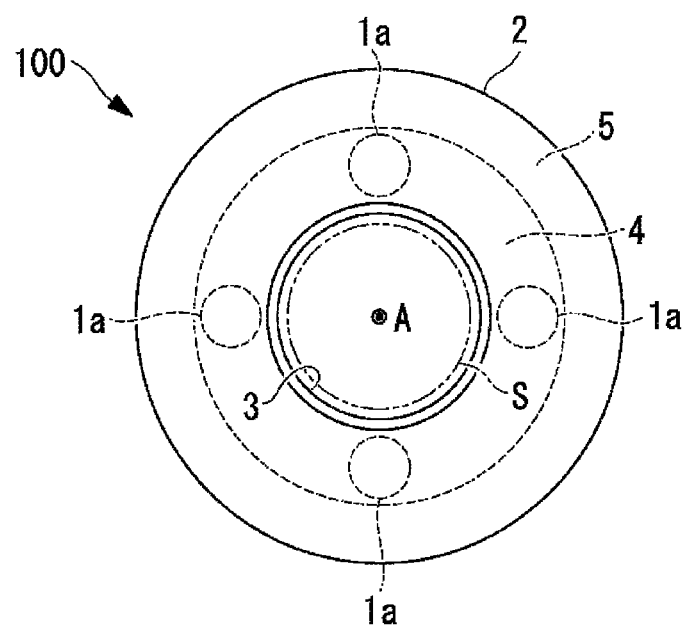
FIG. 2 is a front view of the illumination device, showing a modification of the shape of the output ends of the light output units in FIGS. 1A and 1B.
Figure 3:
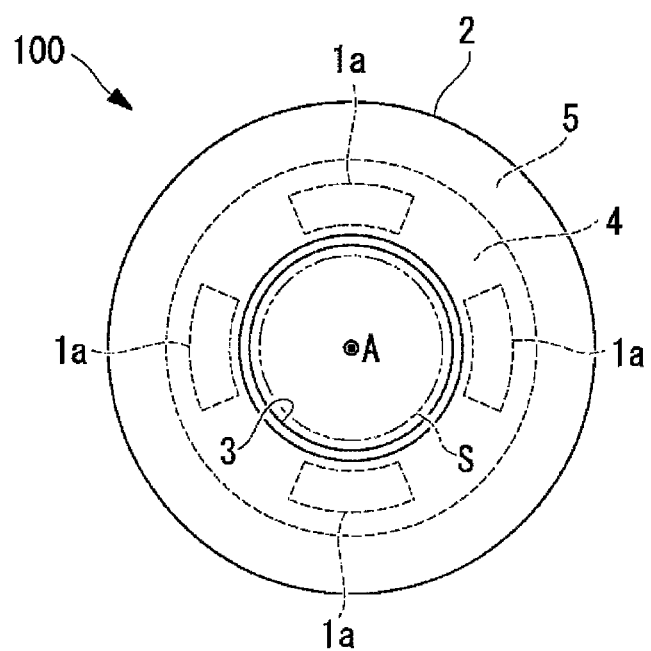
FIG. 3 is a front view of the illumination device, showing another modification of the shape of the output ends of the light output units in FIGS. 1A and 1B.

Although FIGS. 1A and 1B illustrate four light output units 1 arranged at regular intervals on a circumference centered on the observation optical axis A, the arrangement and number of light output units 1 may be changed, as appropriate. The light output units 1 may be, for example, small solid-state light sources such as LEDs and lasers, rather than fiber bundles. The shape of the output ends 1a may also be changed, as appropriate. As shown in FIGS. 2 and 3, the output ends 1a may be circular or annular-sector-shaped, and they may also have other shapes, including ovals and polygons other than rectangles. This improves the design flexibility of the light output unit.

The optical member 2 is disposed such that the central axis thereof (predetermined axis) is substantially in line with the observation optical axis (predetermined axis) A. A typical image-capturing optical system installed in the endoscope includes a plurality of lenses arranged in line along the observation optical axis A and a cylindrical frame holding the plurality of lenses inside. The optical member 2 is disposed around the outer circumferential surface of the frame.

The optical member 2 has a layered structure in which two layers 4 and 5 are stacked in the radial direction. Specifically, the optical member 2 includes a light guide layer 4 located inside in the radial direction and a diffusion layer 5 located outside the light guide layer 4 in the radial direction and at the distal end of the light guide layer 4 and covering the outer surface of the light guide layer 4. The outer circumferential surface of the light guide layer 4 is joined to the inner circumferential surface of the diffusion layer 5 so that the illumination light can travel between the light guide layer 4 and the diffusion layer 5.

The light guide layer 4 is made of a light guide material through which the illumination light propagates. Examples of light guide materials include plastic materials such as acrylic and ZEONOR.

It is desirable that the diffusion layer 5 contain a same light guide material as the light guide material that forms the light guide layer 4 and a diffusion material that diffuses the illumination light. The diffusion material is dispersed and supported at substantially uniform density in the light guide material, which serves as a matrix. Examples of diffusion materials include titanium oxide.

Figure 4:
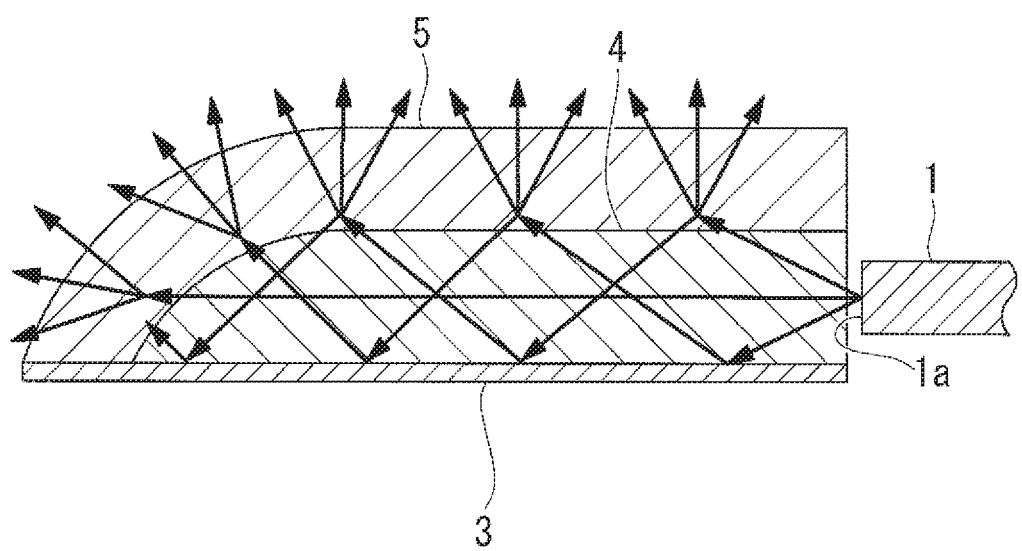
FIG. 4 illustrates the behavior of rays in the optical member in FIGS. 1A and 1B.

As shown in FIG. 4, the rays contained in the illumination light entering the proximal-end surface of the optical member 2 travel in various directions depending on the angle of incidence, and most rays enter the diffusion layer 5 under the reflection effect of the reflective layer 3, described later. The arrows in FIG. 4 indicate the rays contained in the illumination light and the directions in which the rays travel.

While the illumination light entering the diffusion layer 5 is guided through the diffusion layer 5, the illumination light is substantially isotropically diffused by repeated refraction due to the difference in refractive index between the light guide material and the diffusion material and is thereby converted into substantially isotropically scattered light. Nearly all of the illumination light that has been converted into substantially isotropically scattered light is output to the outside from the surfaces of the diffusion layer 5 that are exposed to the outside, i.e., the distal-end surface and the outer circumferential surface, under the reflection effect of the reflective layer 3, described later. Thus, the illumination light output toward the front with respect to the observation optical axis A from the distal-end surface of the diffusion layer 5 mainly illuminates the forward field of view of the observation optical system, whereas the illumination light output in the radial directions with respect to the observation optical axis A from the outer circumferential surface of the diffusion layer 5 mainly illuminates the side field of view of the observation optical system over the entire circumference thereof.

The distal-end surface of the optical member 2 has a conical shape that is smoothly continuous with the outer circumferential surface and that becomes gradually narrower toward the distal end, preferably a round conical shape. This allows the illumination light output from the distal-end surface and the outer circumferential surface to have uniform intensity at each angle and thus allows a wide field of view to be illuminated with uniform brightness at each position, thus providing good illumination performance.

The reflective layer 3 has a high reflectance for the illumination light and is disposed inside the inner circumferential surface of the optical member 2 in the radial direction and adjacent to the inner circumferential surface of the optical member 2. The reflective layer 3 may be a sheet or pipe fixed to the inner circumferential surface of the optical member 2. The reflective layer 3 may be adjacent to the optical member 2 with an air layer therebetween or may be fixed to the optical member 2 with an optical adhesive having substantially the same refractive index as the optical member 2. Alternatively, the reflective layer 3 may be a reflective film formed on the inner circumferential surface of the optical member 2. The illumination light output from the inner circumferential surface of the optical member 2 is reflected back into the optical member 2 by the reflective layer 3; thus, nearly all of the illumination light entering the optical member 2 along the observation optical axis A is output from the distal-end surface and outer circumferential surface of the optical member 2 and contributes to the illumination of the forward and side fields of view. This provides high illumination efficiency.

The operation of the thus-configured illumination device 100 will now be described.

In the illumination device 100 according to this embodiment, the illumination light directed from the output ends 1a of the light output units 1 into the light guide layer 4 of the optical member 2 enters the diffusion layer 5 located outside the light guide layer 4 and is guided through the diffusion layer 5 while being diffused in various directions. Some of the rays contained in the illumination light are output from the distal-end surface or outer circumferential surface of the diffusion layer 5. Other rays contained in the illumination light enter the light guide layer 4 again from the inner circumferential surface of the diffusion layer 5, travel in a straight line through the light guide layer 4, are output from the inner circumferential surface of the light guide layer 4, are reflected back toward the diffusion layer 5 by the reflective layer 3 disposed between the light guide layer 4 and the image-capturing optical system, and travel in a straight line again to enter the diffusion layer 5; thus, they are repeatedly diffused by the diffusion layer 5 and reflected by the reflective layer 3 until they are output from the distal-end surface or outer circumferential surface of the diffusion layer 5. In this way, the illumination light directed from the light output units 1 into the optical member 2 can simultaneously illuminate the forward and side fields of view of the observation optical system with sufficient brightness and little intensity loss.

The illumination light that has been converted into isotropically scattered light by nearly complete diffusion (Lambertian scattering) in the diffusion layer 5 is output in various directions from the diffusion layer 5. Since the distal-end surface and the outer circumferential surface are smoothly continuous in shape, there is no discontinuous change in brightness between the illumination light output from the distal-end surface and the illumination light output from the outer circumferential surface. This allows illumination with uniform brightness over a wide angular range, i.e., 180° or more.

In this case, the illumination device 100 according to this embodiment is a cylindrical device disposed in a thin space around the image-capturing optical system installed in the endoscope so as to be coaxial with the image-capturing optical system and has a layered structure with a sufficiently small size in the radial direction of the endoscope. The illumination device 100 can thus be built into the distal end of the endoscope with little increase in the tip diameter of the endoscope. Specifically, the illumination device 100 built into the distal end of the endoscope increases the tip diameter of the endoscope only by the thickness of the cylindrical optical member 2 and the reflective layer 3. The illumination device 100 is therefore advantageous in that it is suitable for use with thin endoscopes.

The illumination light is also diffused backward (in the drawings, in the direction from left to right) with respect to the observation optical axis A in the diffusion layer 5. Specifically, a portion of the illumination light diffused by the diffusion layer 5, particularly near the proximal-end surface of the optical member 2, is output from the proximal-end surface of the optical member 2, which results in a loss in intensity of the illumination light. According to this embodiment, the light guide layer 4, which has no diffusion effect on the illumination light, is disposed at the inner side in the radial direction, where the illumination light is directed from the output ends 1a. This is advantageous in reducing the illumination light output from the optical member 2 backward with respect to the observation optical axis A and thereby achieving a higher illumination efficiency.

Figure 5A:
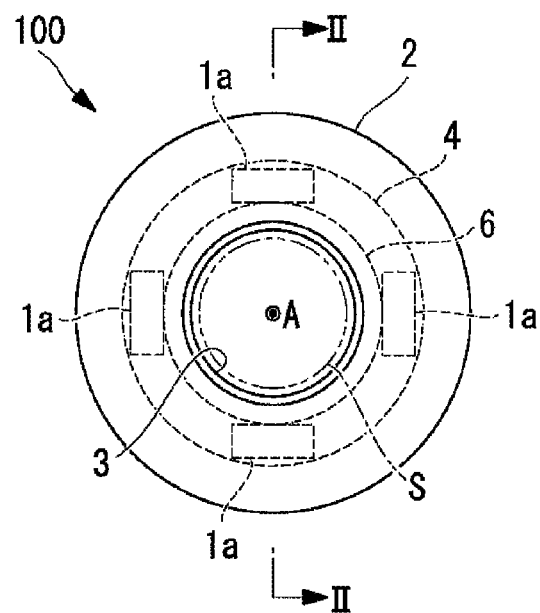
FIG. 5A is a front view of the illumination device, showing a modification of the optical member in FIGS. 1A and 1B.
Figure 5B:
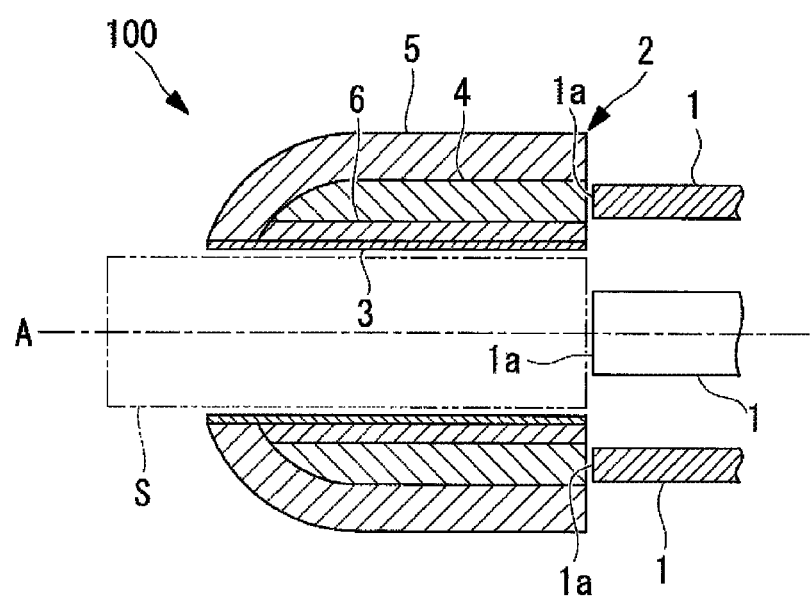
FIG. 5B is a longitudinal sectional view, taken along line II-II, of the illumination device in FIG. 5A.

In this embodiment, the optical member 2 includes only the diffusion layer 5 disposed outside the light guide layer 4; as shown in FIGS. 5A and 5B, the optical member 2 may include another diffusion layer 6 disposed inside the light guide layer 4 in the radial direction between the light guide layer 4 and the reflective layer 3, thereby forming a structure in which the three layers 4, 5, and 6 are stacked on top of each other in the radial direction.

Figure 6:
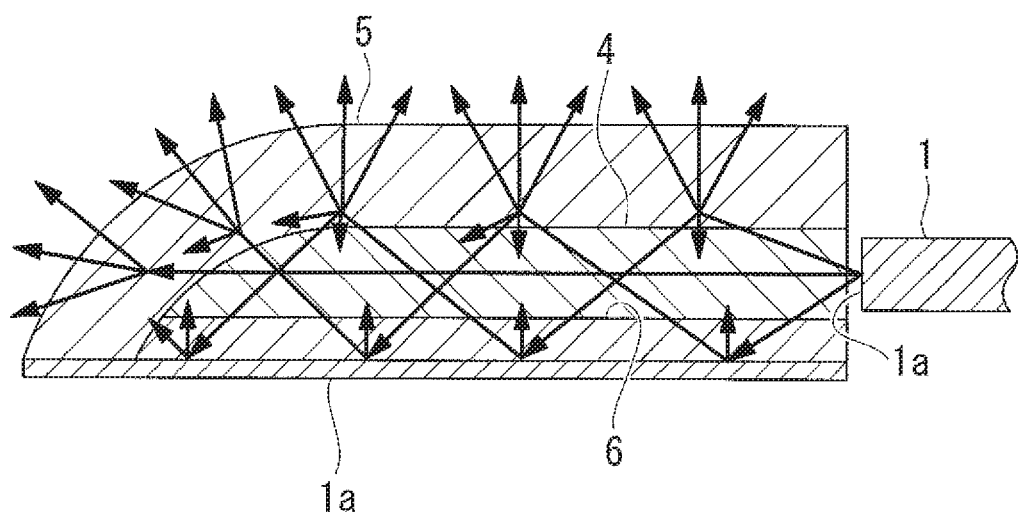
FIG. 6 illustrates the behavior of rays in the optical member in FIGS. 5A and 5B.

As shown in FIG. 6, the illumination light behaves in the thus-configured optical member 2 substantially in the same way as in the optical member 2 in FIGS. 1A and 1B. Again, the light guide layer 4 disposed at the position where the illumination light is directed from the output ends 1a can improve the illumination efficiency.

{Second Embodiment}

An illumination device 200 according to a second embodiment of the present invention will now be described with reference to FIGS. 7 and 8. In this embodiment, the elements that differ from those of the first embodiment described above are mainly described, whereas the same elements as in the first embodiment are labeled with the same reference signs and are not described.

Figure 7:
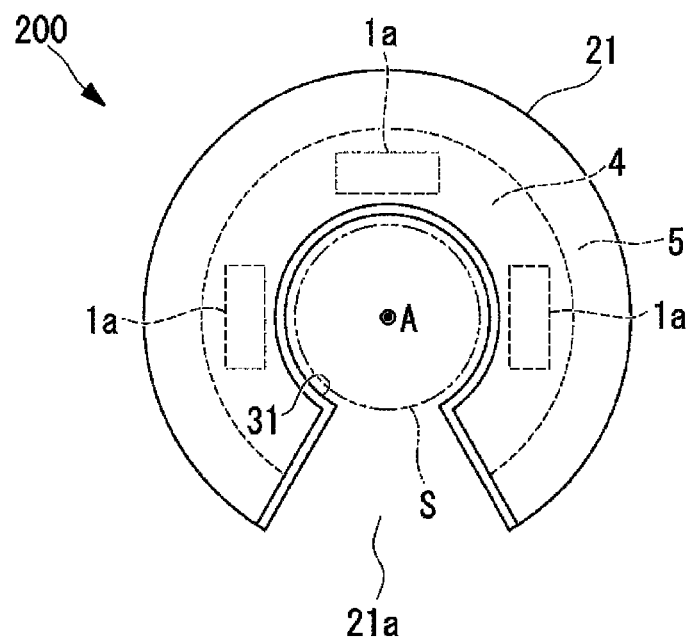
FIG. 7 is a front view showing the overall configuration of an illumination device according to a second embodiment of the present invention.
Figure 8:
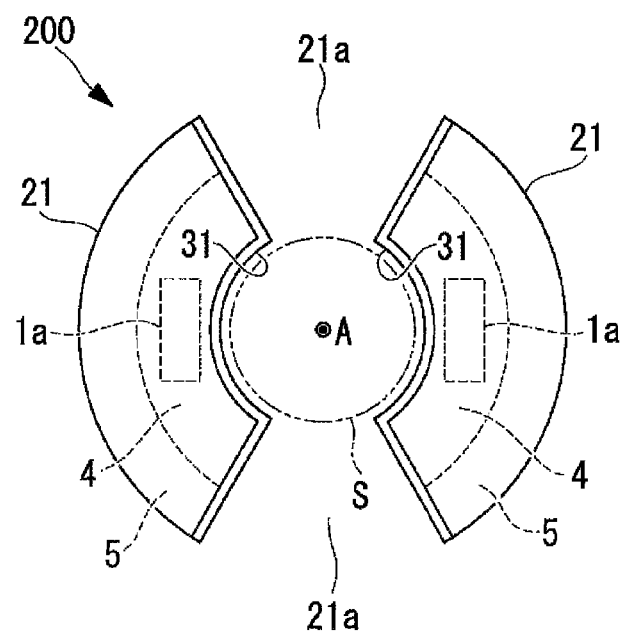
FIG. 8 is a front view of the illumination device, showing a modification of the optical member in FIG. 7.

As shown in FIG. 7, the illumination device 200 according to this embodiment differs from the illumination device 100 according to the first embodiment mainly in that the illumination device 200 includes an optical member 21 having an approximately C-shaped transverse cross-section formed by removing a portion extending in the circumferential direction, rather than the optical member 2 extending over the entire circumference thereof.

A cutout 21a formed by removing, in the longitudinal direction, a portion of the optical member 21 extending in the circumferential direction has an annular-sector-shaped transverse cross-section. The remaining configuration and operation of the optical member 21 are similar to those of the optical member 2 in the first embodiment.

A reflective layer 31 is provided on the inner circumferential surface of the optical member 21, as the reflective layer 3 is in the first embodiment, to reflect the illumination light output from the inner circumferential surface back into the optical member 21. Preferably, the reflective layer 31 is also provided on the sectional surfaces of the optical member 21 exposed in the cutout 21a to reflect the illumination light output from the sectional surfaces back into the optical member 21. The remaining configuration and operation of the reflective layer 31 are similar to those of the reflective layer 3 in the first embodiment.

Various components are dispose around the image-capturing optical system for design reasons. The illumination device 200 according to this embodiment allows such components to be installed in the space formed by the cutout 21a, which is advantageous in providing a more versatile structure. Another advantage is that, as in the first embodiment, the illumination device 200 allows effective and efficient illumination over a wide angular range, i.e., 180° or more, and is suitable for use with thin endoscopes.

In this embodiment, the shape and number of cutouts 21a may be changed, as appropriate. For example, the optical member 21 may be divided into a plurality of optical members 21 in the circumferential direction by forming a plurality of cutouts 21a in the circumferential direction such that the plurality of optical members 21 are arranged in the circumferential direction. In this case, each optical member 21 is a pillar member having a substantially horseshoe-shaped transverse cross-section perpendicular to the observation optical axis A and a side surface curved about the observation optical axis A at the inner side in the radial direction. FIG. 8 illustrates an example where the optical member 21 is divided into two members by forming two cutouts 21a in the circumferential direction. As shown in FIGS. 2 and 3, the output ends 1a of the light output units 1 in this embodiment may have shapes other than rectangles.

As shown in FIGS. 5A and 5B, the optical member 21 in this embodiment may include another diffusion layer 6.

{Third Embodiment}

An illumination device 300 according to a third embodiment of the present invention will now be described with reference to FIGS. 9A to 10B. In this embodiment, the elements that differ from those of the first and second embodiments described above are mainly described, whereas the same elements as in the first and second embodiments are labeled with the same reference signs and are not described.

Figure 9A:
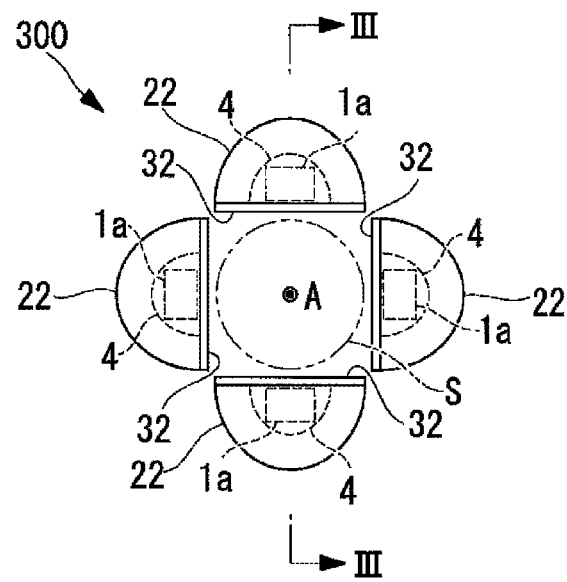
FIG. 9A is a front view showing the overall configuration of an illumination device according to a third embodiment of the present invention.
Figure 9B:
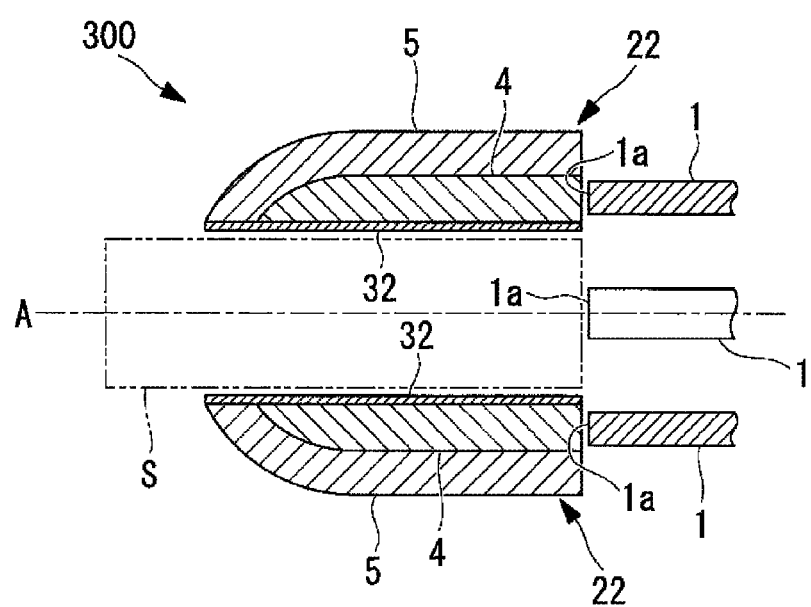
FIG. 9B is a longitudinal sectional view, taken along line III-III, of the illumination device in FIG. 9A.

As shown in FIGS. 9A and 9B, the illumination device 300 according to this embodiment differs from the illumination devices 100 and 200 according to the first and second embodiments mainly in that the illumination device 300 includes a plurality of (in this example, four) optical members 22 arranged substantially at regular intervals in the circumferential direction centered on the observation optical axis A, rather than the cylindrical optical members 2 and 21, and that the illumination device 300 includes four units each composed of an optical member 22, a reflective layer 32, and a light output unit 1.

Each optical member 22 is a substantially semicircular pillar member having a flat side surface at the inner side in the radial direction and a curved side surface at the outer side in the radial direction. The remaining configuration and operation of the optical members 22 are similar to those of the optical member 2 in the first embodiment.

The reflective layers 32 are provided on the flat side surfaces of the optical members 22 and have a flat shape. The remaining configuration and operation of the reflective layers 32 are similar to those of the reflective layer 3 in the first embodiment.

The thus-configured illumination device 300 according to this embodiment, which includes the four separate optical members 22, is advantageous in that the flat side surfaces of the optical members 22 can be processed in any direction during the process of forming the reflective layers 32 on the optical members 22 and that the reflective layers 32, which have a flat shape, are easier to form than the reflective layers 3 and 31 described above. Another advantage is that, as in the first embodiment, the illumination device 300 allows effective and efficient illumination over a wide angular range, i.e., 180° or more, and is suitable for use with thin endoscopes.

Figure 10A:
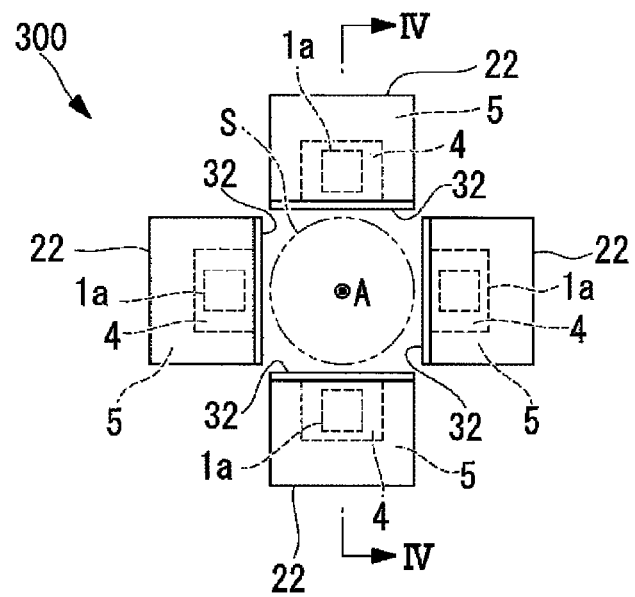
FIG. 10A is a front view of the illumination device, showing a modification of the shape of the optical member in FIGS. 9A and 9B.
Figure 10B:
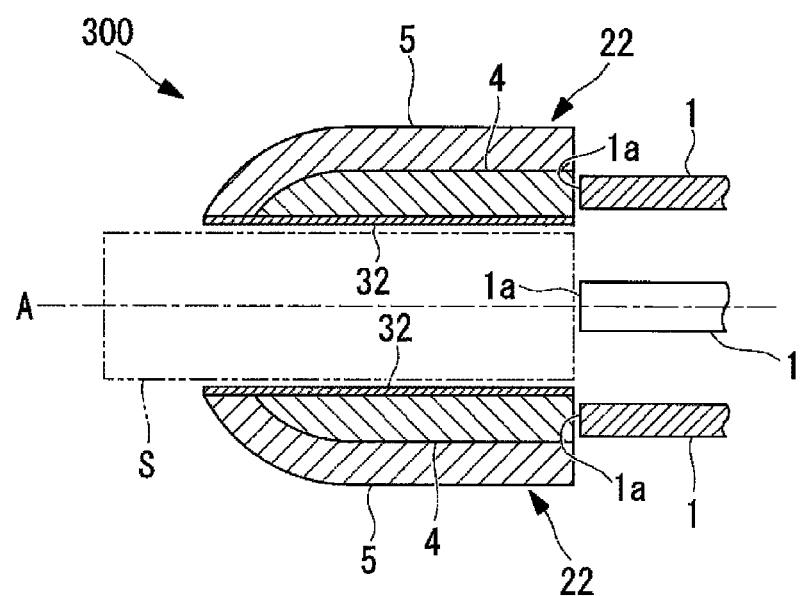
FIG. 10B is a longitudinal sectional view, taken along line IV-IV, of the illumination device in FIG. 10A.

In this embodiment, the optical members 22 may have any pillar shape with a flat side surface at the inner side in the radial direction. For example, as shown in FIGS. 10A and 10B, the optical members 22 may have a quadrangular prism shape with a rectangular transverse cross-section.

As shown in FIGS. 2 and 3, the output ends 1a of the light output units 1 in this embodiment may have shapes other than rectangles.

As shown in FIGS. 5A and 5B, the optical members 22 in this embodiment may include another diffusion layer 6.

{Fourth Embodiment}

An illumination device 400 according to a fourth embodiment of the present invention will now be described with reference to FIGS. 11A to 11B. In this embodiment, the elements that differ from those of the first to third embodiments described above are mainly described, whereas the same elements as in the first to third embodiments are labeled with the same reference signs and are not described.

Figure 11A:
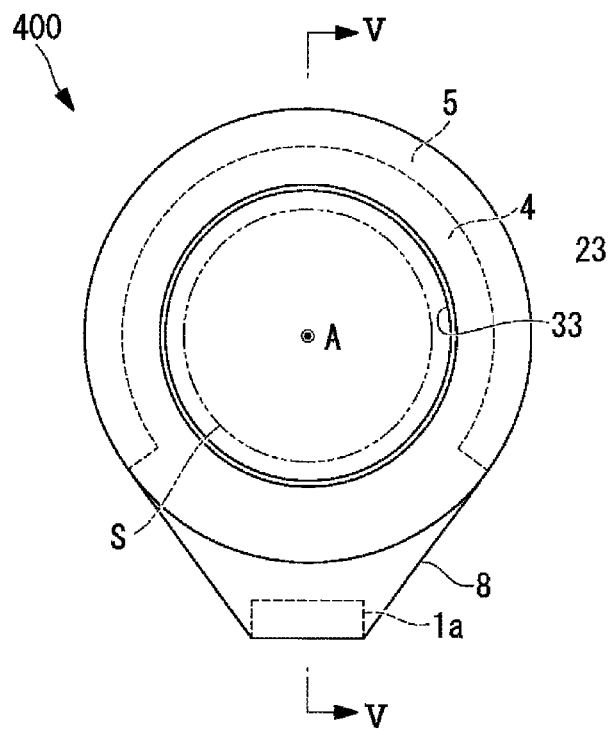
FIG. 11A is a front view showing the overall configuration of an illumination device according to a fourth embodiment of the present invention.
Figure 11B:
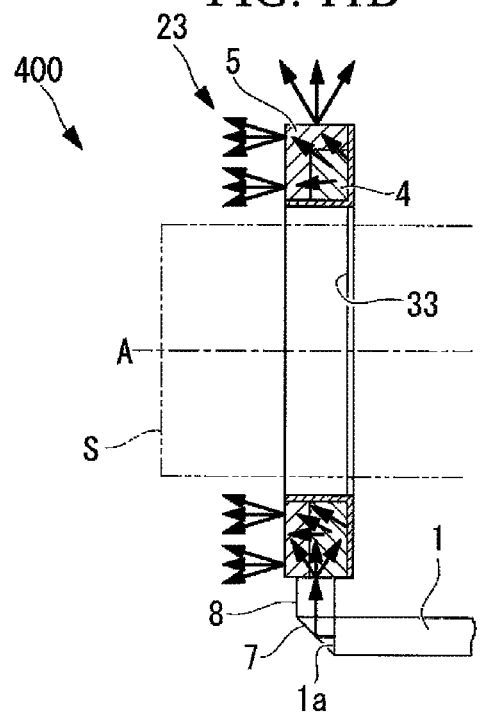
FIG. 11B is a longitudinal sectional view, taken along line V-V, of the illumination device in FIG. 11A.

As shown in FIGS. 11A and 11B, the illumination device 400 according to this embodiment differs from the illumination devices 100 to 300 according to the first to third embodiments mainly in that the light output unit 1 directs illumination light into the side of an optical member 23, rather than into the proximal end of the optical member 2, 21, or 22.

In this embodiment, the optical member 23 is a ring-shaped member having a smaller size in the observation optical axis A direction than the optical member 2. The remaining configuration of the optical member 23 is similar to that of the optical member 2 in the first embodiment except that the diffusion layer 5 is eliminated in a portion where the illumination light is directed from the output end 1a in the circumferential direction.

Disposed outside the optical member 23 in the radial direction are a deflection prism 7 that deflects the illumination light output parallel to the observation optical axis A from the output end 1a of the light output unit 1 by 900 toward the outer circumferential surface of the optical member 23 and an optical member 8 that joins the output surface of the deflection prism 7 to a portion of the outer circumferential surface of the optical member 23. This allows the illumination light output from the output end 1a to enter at least the light guide layer 4, preferably both the light guide layer 4 and the diffusion layer 5.

A reflective layer 33 is provided on the inner circumferential surface and the proximal-end surface of the ring-shaped optical member 23 and reflects the illumination light output from the inner circumferential surface or the proximal-end surface back into the optical member 23 so that substantially all of the illumination light entering the optical member 23 is output from the distal-end surface (output surface) and the outer circumferential surface (output surface) of the optical member 23. That is, the illumination device 400 according to this embodiment includes, in order from the distal end in the direction along the observation optical axis A, the diffusion layer 5, the light guide layer 4, and the reflective layer 33 in a stack.

In the thus-configured illumination device 400 according to this embodiment, the illumination light output from the output end 1a is deflected by the deflection prism 7 to enter a portion of the outer circumferential surface (side surface) of the light guide layer 4 of the optical member 23 through the optical member 8. As in the first embodiment, the illumination light is converted into substantially isotropically scattered light by the optical member 23 and is output from the distal-end surface and the outer circumferential surface of the optical member 23 under the effect of the reflective layer 33. The illumination light is also guided through the light guide layer 4 and the diffusion layer 5 in the circumferential direction while being repeatedly diffused by the diffusion layer 5 and reflected by the reflective layer 33 and is thereby output from the entire circumference of the optical member 23.

The thus-configured illumination device 400 according to this embodiment is advantageous in that, as in the first embodiment, it allows effective and efficient illumination over a wide angular range, i.e., 180° or more, and is suitable for use with thin endoscopes.

As shown in FIGS. 2 and 3, the output end 1a of the light output unit 1 in this embodiment may have shapes other than rectangles.

As shown in FIGS. 5A and 5B, the optical member 23 in this embodiment may include another diffusion layer 6.

REFERENCE SIGNS LIST

100, 200, 300, 400 illumination device
1 light output unit
1a output end
2, 21, 22, 23 optical member
21a cutout
3, 31, 32, 33 reflective layer
4 light guide layer
5 diffusion layer
6 another diffusion layer
7 deflection prism
8 optical member
A observation optical axis

The invention claimed is:
1. An illumination device comprising:
a light output unit having an output end that outputs illumination light;
an optical member that is disposed in a circumferential direction centered on a predetermined axis and that receives the illumination light from the output end and outputs the illumination light from a surface thereof; and
a reflective layer that is provided adjacent to a surface of the optical member at an inner side in a radial direction and that reflects the illumination light outward in the radial direction,
wherein the optical member comprises a light guide layer and a diffusion layer located outside the light guide layer in the radial direction and at one end of the light guide layer facing away from the output end of the light output unit in a direction along the predetermined axis, the light guide layer receives the illumination light from the output end and guides the illumination light, and the diffusion layer receives the illumination light from the light guide layer and guides the illumination light while diffusing the illumination light.

2. The illumination device according to claim 1, wherein the output end is circular, oval, polygonal, or annular-sector-shaped.

3. The illumination device according to claim 2, wherein the optical member is a substantially cylindrical member having a cutout formed by removing, in a longitudinal direction, a portion extending in a circumferential direction.

4. The illumination device according to claim 3, comprising a plurality of the optical members arranged in a circumferential direction centered on the axis,
wherein each optical member is a substantially horseshoe-shaped pillar member having a side surface curved about the predetermined axis at the inner side in the radial direction, and
the reflective layer is provided on the curved side surface.

5. The illumination device according to claim 2, comprising a plurality of the optical members arranged in the circumferential direction centered on the axis,
wherein each optical member is a pillar member having a flat side surface at the inner side in the radial direction, and
the reflective layer is provided on the flat side surface.

6. The illumination device according to claim 2, wherein the light guide layer comprises a light guide material through which the illumination light propagates; and
the diffusion layer comprises a light guide material that is the same as the light guide material that forms the light guide layer and a diffusion material that diffuses the illumination light.

7. The illumination device according to claim 2, wherein the optical member has an outer circumferential surface and a distal-end surface having a conical shape that is smoothly continuous with the outer circumferential surface and that becomes gradually narrower toward a distal end.

8. The illumination device according to claim 1, wherein the optical member is a substantially cylindrical member having a cutout formed by removing, in a longitudinal direction, a portion extending in a circumferential direction.

9. The illumination device according to claim 8, comprising a plurality of the optical members arranged in a circumferential direction centered on the axis,
wherein each optical member is a substantially horseshoe-shaped pillar member having a side surface curved about the predetermined axis at the inner side in the radial direction, and
the reflective layer is provided on the curved side surface.

10. The illumination device according to claim 1, comprising a plurality of the optical members arranged in the circumferential direction centered on the axis,
wherein each optical member is a pillar member having a flat side surface at the inner side in the radial direction, and
the reflective layer is provided on the flat side surface.

11. The illumination device according to claim 1, wherein the light guide layer comprises a light guide material through which the illumination light propagates; and
the diffusion layer comprises a light guide material that is the same as the light guide material that forms the light guide layer and a diffusion material that diffuses the illumination light.

12. The illumination device according to claim 1, wherein the optical member has an outer circumferential surface and a distal-end surface having a conical shape that is smoothly continuous with the outer circumferential surface and that becomes gradually narrower toward a distal end.

* * * * *